Figure 1:
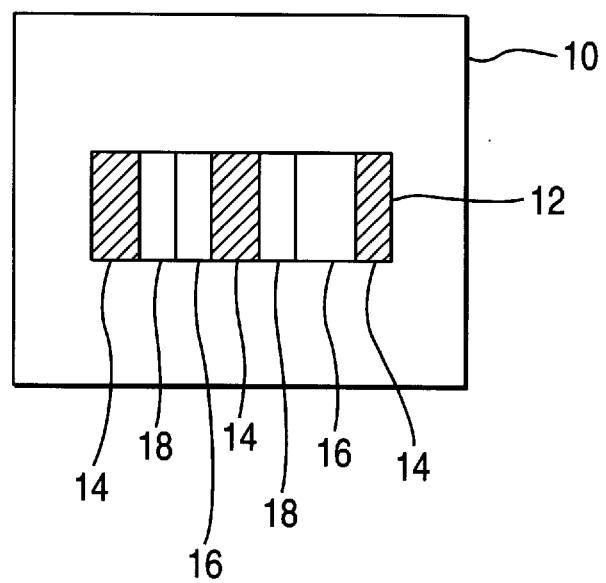

United States Patent

Beale et al.

[11] Patent Number: 5,854,673
[45] Date of Patent: Dec. 29, 1998

[54] METHOD OF AUTHENTICATING WATERMARKED PAPER

[75] Inventors: Marc I J Beale, Malvern; David R Dinn, Leatherhead, both of Great Britain

[73] Assignees: Secretary of State for Defence in her Britannic Majesty's Government of the United Kingdom of Great Britain & Northern Ireland of Defence; Evaluation Research Agency, both of United Kingdom

[21] Appl. No.: 849,383

[22] PCT Filed: Dec. 7, 1995

[86] PCT No.: PCT/GB95/02855

§ 371 Date: Jun. 3, 1997

§ 102(e) Date: Jun. 3, 1997

[87] PCT Pub. No.: WO96/18978

PCT Pub. Date: Jun. 20, 1996

[30] Foreign Application Priority Data

Dec. 14, 1994 [GB] United Kingdom ............... 9425232

[51] Int. Cl.⁶ .................................................. G06K 9/74
[52] U.S. Cl. ......................... 356/71; 356/51; 250/358.1; 250/556
[58] Field of Search .................. 356/51, 71; 250/358.1, 250/556

[56] References Cited

U.S. PATENT DOCUMENTS

| 4,296,326 | 10/1981 | Haslop et al. ............................. 356/71 |
| 4,481,418 | 11/1984 | Vanzetti et al. ......................... 250/338 |
| 4,608,598 | 8/1986 | Murakami et al. ....................... 358/113 |

FOREIGN PATENT DOCUMENTS

| 0348742 A3 | 6/1989 | European Pat. Off. . |
| 0381550 A1 | 1/1990 | European Pat. Off. . |
| 2 168 494 | 6/1986 | United Kingdom . |
| 2 199 942 | 7/1988 | United Kingdom . |
| 2264779 | 9/1993 | United Kingdom . |
| WO87/00632 | 1/1987 | WIPO . |
| WO90/08311 | 7/1990 | WIPO . |

*Primary Examiner*—Richard A. Rosenberger
*Attorney, Agent, or Firm*—Nixon & Vanderhye

[57] ABSTRACT

A method of authenticating watermarked paper comprises the steps of transiently heating a first surface (50) of a watermarked sheet of paper (40) using a hot air source (22); forming a thermal image of the watermark (42) using a thermal imager (30); and analyzing the thermal image to determine whether or not the watermarked paper is authentic. The evolution of the thermal image with time is characteristic of the watermark and is dependent on the local thermal mass of the paper in the region of the watermark.

12 Claims, 3 Drawing Sheets

METHOD OF AUTHENTICATING WATERMARKED PAPER

The invention relates to a method of authenticating watermarked paper. Watermarks are have been used as a security feature for several centuries. They provide an easily identifiable image to the unaided eye of a viewer. Their value as a security feature derives from the fact that a watermark is difficult to either fabricate or simulate. A true watermark must be formed during the manufacture of the paper and requires large and expensive facilities not available to the small-scale counterfeiter Simulation by some other means that looks convincing under close scrutiny is also difficult.

Watermark inspection is generally performed by a human operator, often in a rushed and haphazard manner with no equipment to assist viewing or authentication of the image. Watermarks are often partially obscured by printing on one or both sides of the document making authentication more difficult. The anti-counterfeiting potential of a watermark is therefore not fully realised in practice.

A watermark generally comprises areas of high and low density paper of uniform thickness which are introduced during the paper making process. The density variations may be substantial typically spanning a factor of two. The watermark may incorporate grey-scale and the best examples have significant artistic merit. The spatial resolution is such that feature sizes smaller that 1 mm can be readily resolved.

Watermarks were originally developed to be viewed by the unaided human eye. They are generally not easily seen in reflected light but are readily visible in transmitted light. The most obvious route to machine reading watermarks is therefore conventional optical imaging. For example the watermark may be illuminated with white light or light of a specific wavelength and imaged using a silicon charge coupled device (CCD) camera. A low cost authentication system can readily be designed on the basis of such optical imaging but, if the aim is to obtain a high contrast image of the watermark unobscured by printed matter, then its usefulness would be restricted. Furthermore, any authentication process based on the use of transmitted light must contend with ease with which the counterfeiter can use simple printing technology to simulate a watermark and thereby defeat an authentication system.

Optical imaging may be extended to imaging with wavelengths outside the visible spectrum in the UV or the IR. Although good image contrast may be obtained using a broad-band UV source, any printed matter on the item is included in the image and complicates its analysis. In the near-IR, dye-based printing inks are transparent and an image of the watermark without any printed features may be obtained. However carbon-containing inks do absorb in this waveband and confuse the analysis.

Banknote authentication systems are known which incorporate infra-red sources to measure the optical transmission coefficient of the notes in the infra-red part of the spectrum. Swedish Patent Number SE 451 041 describes a system in which infra-red radiation of wavelength 900–1600 nm is transmitted through a banknote and the intensity of the transmitted radiation is measured by infra-red detectors. Norwegian Patent No. 922387 describes a system for obtaining a two-dimensional image of a watermark based on infra-red transmission measurements of radiation of wavelength between 2 and 12 $\mu$m.

One standard method of revealing watermarks in a research environment is to take a radiograph using an X-ray plate and a beta radiation source. This method forms an image based on the local variations in density and hence radiation absortion power. The layers of ink being relatively thin, have little or no visible effect on the image. The imaging process has very high resolution and yields an image with impressive clarity. This approach is not viable for wide-spread use due to radiation hazards and due to the time taken to process the plate or due to the high cost of an alternative solid state large area X-ray detector.

International Patent Application Number PCT/NO86/00052 having an International Publication Number WO 87/00632 describes a system which for checking whether an object, for example a bank note has a set of properties which warrants that the object is genuine. The system described therein generally comprises a means for heating a localised are of the object and a means for measuring the temperature of the area at a single instant in time which is a certain period of time after the area had been heated. This period of time is governed by either moving the object relative to a source of heat and a thermal detector or moving the source and detector relative to the object a known distance at a certain velocity. The relative velocity must be such that the relative velocity is higher than the thermal diffusion coefficient. The system thus depends upon variations in diffusion coefficient to generate a characteristic thermal signal at a single fixed time after a heat source has been applied.

Mr Jan Waaler of the Norgers Bank presented a paper at the Currency Automation Conference May 3–6, 1992, San Francisco, Calif., which described a bank note authentication system similar to that described in the aforementioned International Patent Application No. PCT/NO86/00052. This system also made a single measurement of the temperature of a bank note a known interval of time after a heat source had been applied.

It is an object of the invention to provide an alternative method of authenticating watermark containing paper.

The present invention provides a method of authenticating watermarked paper comprising the steps of:
  (i) heating a first surface of a region of the paper containing a watermark,
  (ii) measuring the region's temperature, and
  (iii) analysing the measurements to determine whether or not the watermarked paper is authentic, characterized in that a series of measurements are made of the region's temperature in order to determine the thermal response of the paper as a function of time.

In a preferred embodiment the temperature change is measured using a thermal imaging camera arranged to image the region. The camera may be arranged to image a second surface of the region. The watermark region may thus be heated on one side and the temperature change measured from an opposite side of the paper.

The thermal imaging camera may be used to obtain thermal images of the region during a heating cycle when heat is being applied to the first surface and during a cooling cycle when the heat source is switched off. The thermal images obtained during the heating and cooling cycles may be analysed to determine whether or not a positive thermal image is followed by a negative thermal image.

It has been found that a thermal image of a watermark is not strongly influenced by the presence of obscuring printing. The method of the invention utilises variations in the mass per unit area of paper in the area of a watermark. There is a corresponding variation in the thermal mass per unit area. The transient input of thermal energy therefore results in local variations in the temperature corresponding to the appearance of the watermark as seen by an unaided eye. These temperature variations may be detected and processed to provide a thermal image of the watermark.

The detection of the local temperature variations across the watermark differentiates the invention from other systems which detect absorption or transmission within the infra-red part of the spectrum but do not detect the temperature response of the watermark.

Detection of the temperature variation may be implemented by contact or non-contact methods the latter are preferred in this invention. A detector sensitive to infra-red radiation typically within the 3–12 $\mu$m band may be used.

In a further aspect, the invention provides a watermark authentication system for determining whether or not a sheet of paper includes an authentic watermark comprising:

(i) means (22) for heating a region of the sheet of paper:

(ii) means (30) for making temperature measurements of the region of the sheet of paper: and (iii) means for analysing the temperature measurements to determine whether the paper is authentic: characterized in that the means for making temperature measurements is arranged to make a series of measurements of the temperature of the sheet of paper in order to determine the thermal response of the paper as a function of time.

Figure 2:
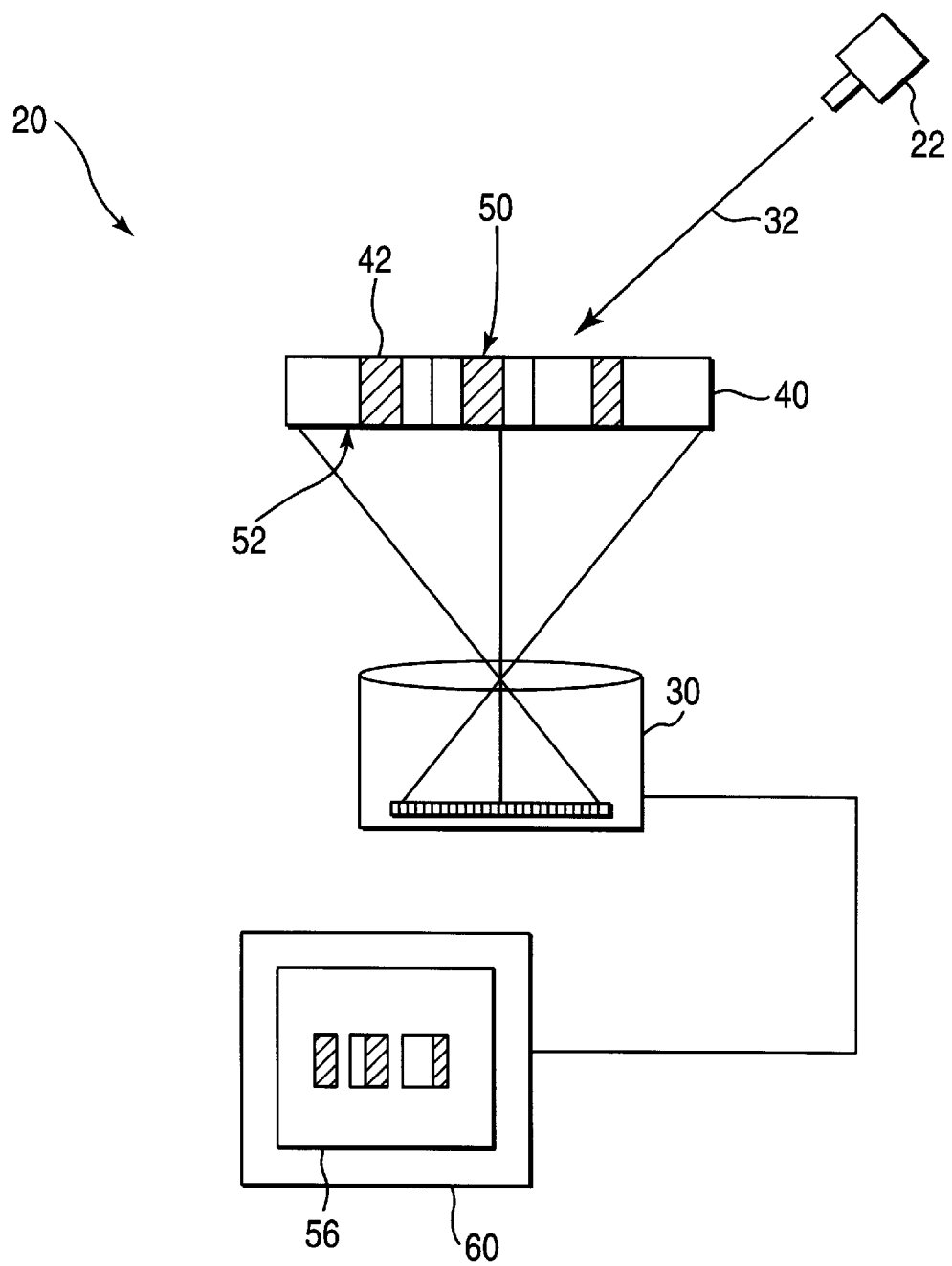

Embodiments of the invention will now be described, by way of example only, with reference to the accompanying drawings in which:

FIG. 1 schematically illustrates a sheet of paper incorporating a watermark;

FIG. 2 schematically illustrates a watermark authentication system; and

FIGS. 3a–3j schematically illustrate the evolution of a thermal image of the FIG. 1 watermark as a function of time.

Referring to FIG. 1 there is shown a schematic illustration of a banknote 10 incorporating a watermark 12. For illustrative convenience the watermark 12 is shown as having rectilinear form. The watermark 12 comprises regions 14 of relatively high paper density, regions 16 of relatively low paper density and regions 18 of medium, or normal paper density.

Referring now to FIG. 2 there is shown a watermark authentication system of the invention indicated generally by 20. The system 20 comprises a hot air source 22 and a thermal imaging pyroelectric vidicon camera system 30 sensitive to radiation of wavelength between 3 $\mu$m and 12 $\mu$m. The thermal imaging system 30 is obtainable from Insight Visions Systems Ltd of Malvern, England, identified as their "80 series"system.

The source 22 is a 1 kW hot air blower. Hot air 32 from the source 22 is directed towards a banknote 40 shown in cross-section incorporating a watermark 42. A first surface 50 of the banknote 40 is warmed by the hot air 32. The thermal imaging system 30 images a second surface 52 of the banknote 40. A thermal image 56 of the banknote 40 is displayed on a video screen 60.

The hot air source 22 and the thermal imaging system are adjusted so as to provide a rate of heating and a camera sensitivity which in combination give a transient positive contrast thermal image of the watermark 42 lasting approximately 1 second as the hot-air 32 warms the banknote 40.

Prior to heating, the bank note 40 has a temperature which is laterally uniform as it is in thermal equilibrium with its surroundings and thus no contrast is visible on the screen 60. On applying the heat a transient image of the watermark 42 is displayed due to the differential heating of the low and high density parts of the watermark. Continued heating of the banknote 40 results in a uniformly high temperature as equilibrium between the heat input to and output from the banknote is established. Under equilibrium conditions, variance in thermal capacity between regions of high and low density does not result in image contrast and the watermark is not displayed. On removing or switching off, the heat source, or applying forced cooling using a source of low temperature air, regions of low thermal capacity cool faster resulting in a negative contrast transient image of the watermark 42 on the monitor 60. The transient nature of these images in combination with the reversal in contrast between heating and cooling cycles is a characteristic of the thermal mass variations within a true watermark which would be difficult to simulate in any other way.

Figure 3:
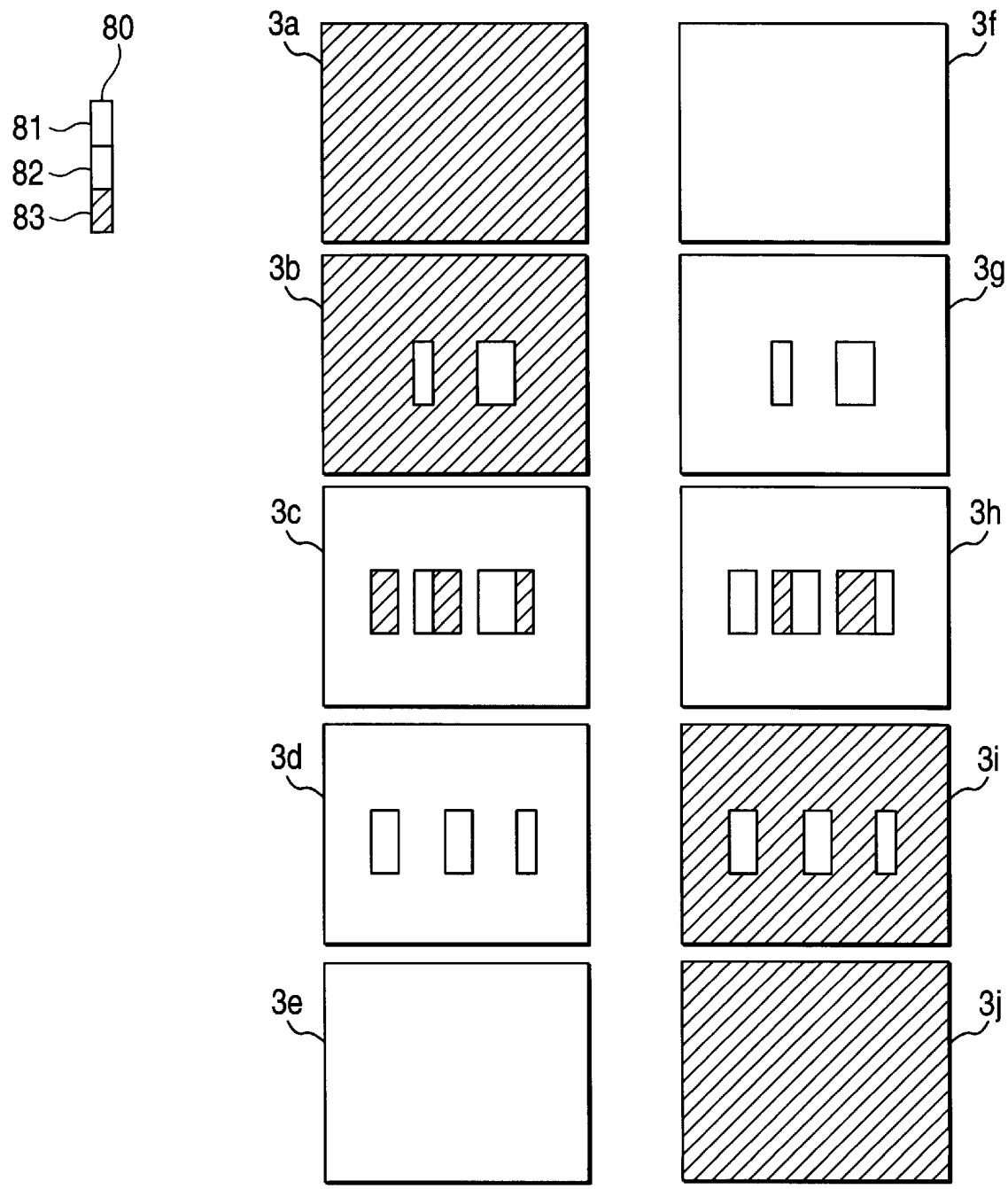

Referring now to FIG. 3 there are shown thermal images or the banknote 10 during a heating and a cooling cycle. As shown in FIG. 3, the transient thermal images have a three level grey scale which is dependent on the temperature of the banknote 10. A key 80 having three shadings 81, 82 and 83, shows the three level grey scale. Shading 81 indicates high temperatures at which the thermal imager is saturated corresponding to a full black level, shading 82 indicates medium temperatures and shading 83 indicates low temperatures corresponding to a full white level. FIGS. 3a to 3e show thermal images indicating the local temperature responses of the banknote 10 after 0.2 second intervals during the heating cycle. In FIG. 3a the banknote starts with a uniformly low temperature in which no contrast is observable. FIG. 3b shows a thermal image of the banknote 10 after 0.2 seconds of heating. In FIG. 3b the areas 16 of the banknote 10 having a low thermal mass have warmed up the quickest and this temperature rise is resolvable by the thermal imager. In FIG. 3c the areas 16 have reached a high temperature the area 18 is at a medium temperature and there is still no temperature rise observable for the areas 14 having the highest density and thermal mass. In FIG. 3d only the areas 14 have not reached a temperature at which the thermal image is saturated. In FIG. 3e the whole of the banknote 10 has reached a temperature at which the thermal imager is saturated.

FIGS. 3f to 3j show thermal images of the banknote 10 at 0.2 second intervals during the cooling cycle after the hot air source has been switched off. In FIG. 3f the whole of the banknote 10 is at a high temperature and there is no image contrast. The areas 16 are the quickest to cool and in FIG. 3g these areas show a medium temperature In FIG. 3h, the areas 16 are at a low temperature whilst the area 18 is at a medium temperature and the areas 14 are still at a high temperature. In FIG. 3i all areas except the areas 14 are at a low temperature with the areas 14 at a medium temperature. In FIG. 3j all the banknote has cooled to a uniform low temperature.

The heating cycle produces a positive thermal image of the watermark, as shown in FIG. 3c and the cooling cycle produces a negative image of the watermark, as shown in FIG. 3h. The evolution of the thermal image of the watermark as a function of time is analysed by an operator of the system 20. If a correct sequence of a positive image followed by a negative image of a watermark having the correct appearance is shown on the video screen 60 the banknote 10 is considered to be authentic in that it has a correct watermark. Alternatively, the analysis of the transient thermal image may be performed by a computer system operating conventional automated image analysis software in which the thermal image is compared with images stored in a data base. The evolution of the thermal image of a watermark is a characteristic property of the watermark which would be exceedingly difficult to counterfeit.

Whilst the system 20 includes the thermal imaging camera system 30, alternative embodiments of the invention may comprise means for measuring the temperature of the paper which do not form a thermal image of the watermark but obtain an integrated measurement of the temporal thermal response of the watermark as a whole In the system 20, a hot air blower 22 is used to heat the banknote 40. Other sources of heat may be used to generate a thermal response in the banknote for example a hot-plate over which the note is passed or a carbon dioxide laser with a defocused beam.

We claim:

1. A method of authenticating watermarked paper comprising the steps of:

(i) changing the temperature of a first surface (50) of a region of the paper containing a watermark (42);

(ii) measuring the region's temperature during the change of temperature; and (iii) analyzing the temperature measurements to determine the thermal response of the paper as a function of time and hence determine whether or not the watermarked paper is authentic.

2. The method of claim 1 wherein the change of temperature is a heating cycle.

3. The method of claim 1 wherein the change of temperature is a cooling cycle.

4. The method of claim 1 wherein the change of temperature is both a heating cycle and a cooling cycle.

5. The method according to claim 1 wherein the temperature change is measured using a thermal imaging camera (30) arranged to image the region.

6. The method according to claim 5 wherein the thermal imaging camera (30) is arranged to image a second surface (52) of the region.

7. The method according to claim 5 further including the step of (iv) analyzing the thermal images to determine whether or not the images measured comprise a positive image followed by a negative image.

8. The method according to claim 7 wherein the analysis of the measurements (iv) includes determining whether or not the thermal images are obtained in a sequence which comprises a substantially contrast free image (3a) followed by a positive image (3c) followed by a second substantially contrast free image (3e) followed by a negative image (3h) followed by a third substantially contrast free image (3j).

9. A watermark authentication system for determining whether or not a sheet of paper includes an authentic watermark comprising: means (22) for changing the temperature of a region of the sheet of paper; means (30) for making temperature measurements of the region of the sheet of paper during the change of temperature; and means for analyzing the temperature measurements to determine the thermal response of the paper as a function of time, and hence determine whether the paper is authentic.

10. The system of claim 9 wherein the means (22) for changing the temperature is a means for heating.

11. The system of claim 9 wherein the means (22) for changing the temperature is a means for cooling.

12. The system of claim 9 wherein the means (22) for changing the temperature is a means for both heating and cooling.

* * * * *

UNITED STATES PATENT AND TRADEMARK OFFICE

CERTIFICATE OF CORRECTION

PATENT NO. : 5,854,673
DATED : December 29, 1998
INVENTOR(S) : BEALE et al

It is certified that error appears in the above-identified patent and that said letters patent is hereby corrected as shown below:

On the title page, correct the second inventor's surname to --OINN--.

Signed and Sealed this

Nineteenth Day of October, 1999

Attest:

Q. TODD DICKINSON

*Attesting Officer*   *Acting Commissioner of Patents and Trademarks*